United States Patent
Piccariello

Patent Number: 5,406,005
Date of Patent: Apr. 11, 1995

[54] METHOD FOR THE PRODUCTION OF D-CHIROINOSITOL

[76] Inventor: Thomas Piccariello, 203 Murphy St., Blacksburg, Va. 24060

[21] Appl. No.: 228,101

[22] Filed: Apr. 15, 1994

[51] Int. Cl.⁶ ............................................. C07C 35/16
[52] U.S. Cl. ................................. 568/833; 568/822; 568/832
[58] Field of Search ........................ 568/822, 832, 833

[56] References Cited

U.S. PATENT DOCUMENTS

| | | | |
|---|---|---|---|
| 2,615,053 | 10/1952 | Artz et al. | 568/833 |
| 3,270,064 | 8/1966 | Inaha et al. | 568/833 |
| 3,288,820 | 11/1966 | Argoundelis et al. | 568/833 |
| 5,091,596 | 2/1992 | Kennington et al. | 568/833 |

FOREIGN PATENT DOCUMENTS 524082  1/1993  European Pat. Off. ............ 568/833

Primary Examiner—Werren B. Lone
Attorney, Agent, or Firm—Janet Sleath; William J. McNichol, Jr.

[57] ABSTRACT

The invention relates to the synthesis of D-chiro-inositol from glucodialdose comprising the steps of condensing glucodialdose by a acylon condensation reaction, protecting the carbon atoms of the 1,2,5 and 6 position, epimerizing the protected carbon atom at position 5, reducing the ketone of the condensed compound and removing the protect groups.

1 Claim, 5 Drawing Sheets

Bn=Benzyl   Bz=Benzoyl   camph=Camphoryl   Tf=Triflyl

Bn=Benzyl  Bz=Benzoyl  camph=Camphoryl  Tf=Triflyl

DMP=dimethoxypropane; pTsOH=p-toluenesulfonic acid

21

METHOD FOR THE PRODUCTION OF D-CHIROINOSITOL

FIELD OF THE INVENTION

A lack of D-chiroinositol, DCI, one of nine stereoisomers of the inositol series, has been implicated in the etiology of insulin resistant diabetes or non-insulin dependant diabetes mellitus (NIDDM). When DCI has been administered to animal models of diabetes it has been shown to lower blood glucose and insulin levels. Use of DCI as a therapeutic agent in the treatment of NIDDM and the insulin resistant condition is expected to service a significant segment of the population. This invention relates to a de novo synthesis of DCI of a quantity and quality suitable for pharmaceutical use. There have been several syntheses reported for DCI. Unfortunately, the most efficient methodologies are not appropriate for this purpose.

In addition to DCI, the stereospecific synthesis of myoinositol and its phosphate(s), an important class of compounds involved in secondary cellular signalling, have proven to be laborious. This invention is also useful in the applied stereospecific syntheses of myoinositol derivatives and other inositol isomers. These inositol derivatives should be applicable to syntheses of higher order carbohydrates as well.

BACKGROUND OF THE INVENTION

DCI has shown promise as a therapeutic agent to treat insulin resistance and those conditions associated with the disease such as NIDDM. Studies on primate models indicate that 1 gram per day is a reasonable dose upon which to base initial forecasts. There are 14 million diagnosed NIDDM patients in the United States. It is estimated that 20% of the general population is genetically predisposed to insulin resistance and therefore it is expected that daily manufacturing capacities for DCI will need to approach megagram quantities.

DCI can be isolated in kilogram quantities from natural sources. One of these sources is the California sugar pine. It has been shown that a 15 weight percent of pinitol (the 3-0 methyl ether of DCI) can be extracted from the sawdust of this tree's stump. Pinitol can easily be converted to DCI in quantitative yield. With a yield of 1 kg/stump, an estimated 35 million stumps per year will be needed to supply the United States market demand with DCI (this calculation does not incorporate the fact that the stump ideally should be aged 5 years or more). Therefore, it is unlikely that the projected demand of DCI will be satisfied through this source.

DCI is also 40% of the antibiotic kasugamycin and is easily cleaved and purified from the antibiotic. Sources for kasugamycin have yet to prove to be economical. Attempts to produce a viable strain of *S. kasugaensis* either by natural selection techniques or fermentation process modifications have yet to yield a desirable result.

There have been several reported syntheses of chiroinositol (or its easily converted methyl ether) and they either entail a series of exhaustive protection/deprotection steps or fail to give the pure D-chiro isomer in a reasonable fashion. Martin-Lomas, et. al., reported a synthesis of 1-0-methyl-D-chiroinositol from methyl glucopyranose (compound 1) utilizing the well-known Ferrier rearrangement. This approach required that the glucose molecule be subjected to a 4-step protection sequence leading to compound 2 which when rearranged yielded the key intermediate compound 3. Converting compound 3 to 1-0-methyl-D-chiroinositol involved four synthetic steps. Demethylation, as described above, would require an additional step for a total synthesis of DCI in 10 steps.

Ozaki and coworkers devised an approach to DCI starting from glucuronolactone (a.k.a. glucurone, compound 4). This synthesis involves a total of 17 steps, involving seemingly unnecessary manipulations and utilizes exotic reagents such as titanium tetrachloride which is the key reagent in the sequence shown in entry 2 of FIG. 1. In 1990, Shen and coworkers synthesized DCI from myoinositol by selectively epimerizing the 3-D position of myoinositol as shown in entry 3 of FIG. 1. This was done in 5 steps, however, one of the steps yielded a relatively small amount of product and another step involved a labor intensive separation of diastereomers.

The last two syntheses of DCI (entry 4 of FIG. 1) reported are similar in that the key step is a *Pseudomonas putida* oxidation of benzene (which generates a meso compound) or chlorobenzene (which generates an optically active compound) to the cyclohexadienediol derivatives 10 and 11. Hudlicky imparted a novel approach to convert 11 to DCI in 4 steps for a total of 5 steps; the final product, however, was contaminated with alloinositol, another of the nine isomers of inositol.

DETAILED DESCRIPTION OF THE INVENTION

A novel methodology to synthesize inososes has been developed wherein a previously unknown intramolecular thiazolium acyloin condensation is utilized. The advantage is that the use of the thiazolium salt allows the acyloin condensation to occur without the need for anhydrous conditions or the use of hazardous and expensive reagents such as sodium metal. A thiazolium salt catalyzed intramolecular acyloin condensation (analogous intermolecular reactions have been reported), and a new method for preparing inosose are disclosed.

Figure 1:
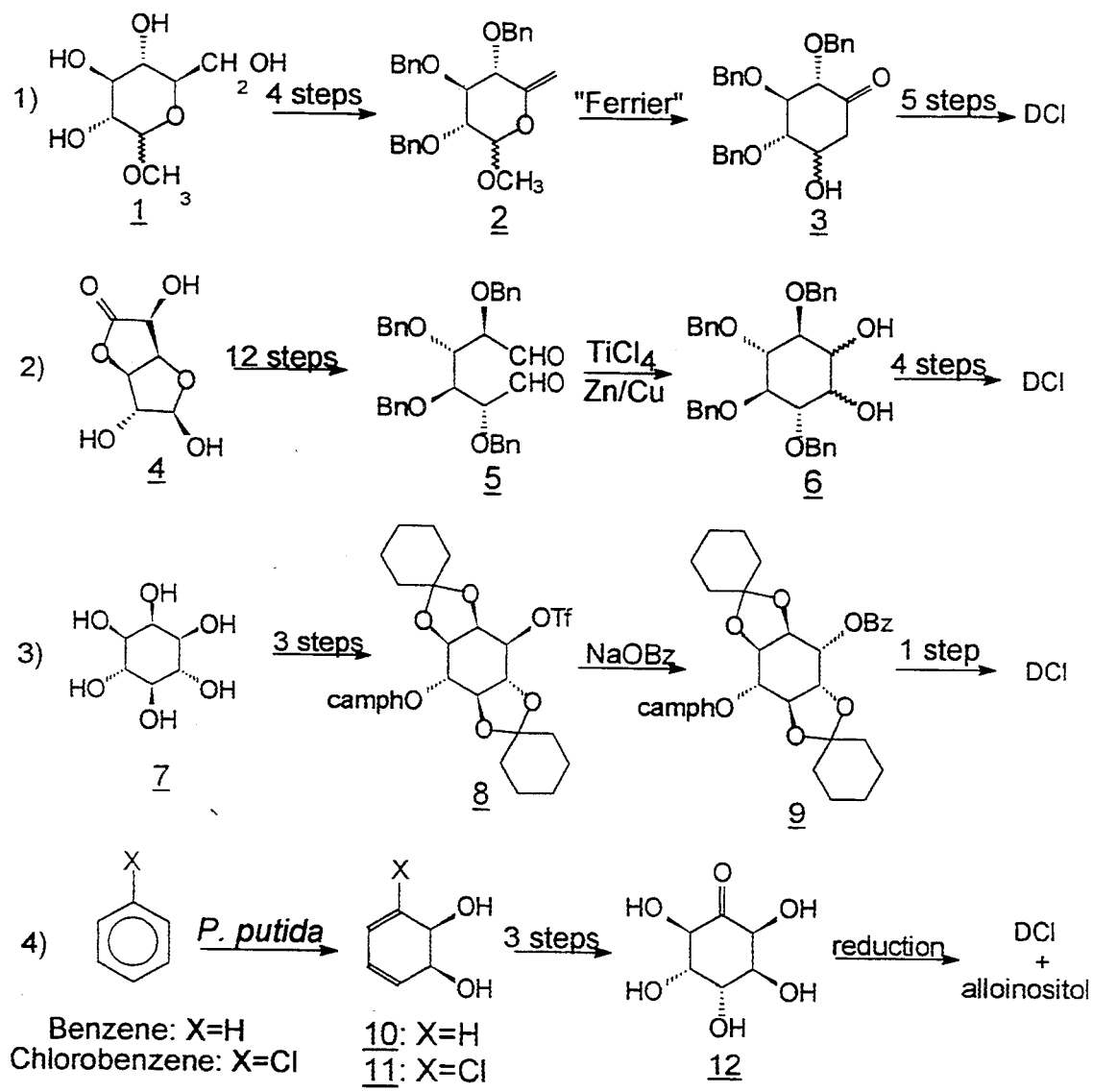
Figure 2:
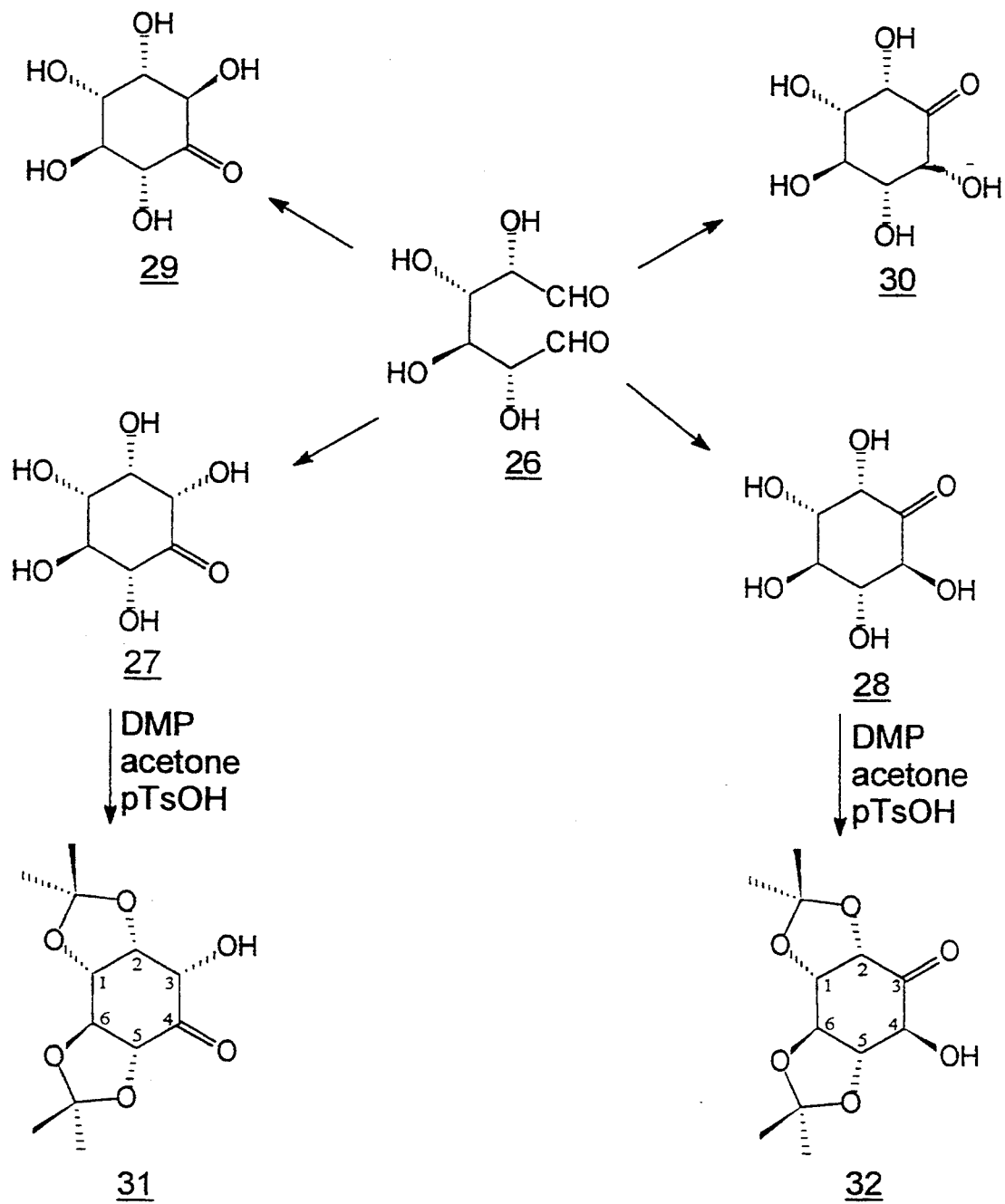

Conversion of glucurone (compound 4) into glucodialdose in quantitative yield has been reported. Dahalloff, W. V. et al., *Synthesis*, 1982 pp. 650–52. Application of the thiazolium catalyzed acyloin condensation as shown in FIG. 2 results in inososes 27 and 28. Formation of 29 and 30 adopt the relatively unstable diaxial configuration. When inososes compounds 27 and 28 are protected as the diacetonide the major products are compounds 31 and 32, respectively.

Refluxing an aqueous mixture of myoinositol and Raney nickel (Sasaki, K. et al., carbohydrate Research, 1987 vol. 166, pp. 171–80) or treating scylloinosose with mild aqueous base yields a mixture of myoinositol, chiroinositol and scylloinositol (plus the other 5 inositols in very low combined yield). The stereoselectivities observed in these reactions are presumably due to the fact that the isomers have adopted the preferred cis-trans configurations about the ring under thermodynamic conditions—a phenomenon most easily understood by recognizing that scylloinositol is the only isomer of the inositol series which is all-trans. In base catalysis, equilibrium is achieved through repetitive deprotonation and protonation from the carbon alpha to the carbonyl carbon until the system is thermodynamically stable, whereas in Raney nickel catalysis, similar effects are realized through a ketone reduction—alcohol oxidation equilibration sequence. Combining both equilibrium conditions in one experiment and imparting these conditions to compound 12 results in a mixture of myoinositol, D-chiroinositol and scylloinositol with little or no alloinositol present.

Subjecting compounds 31 and 32 to mild base followed by refluxing the compounds in Raney nickel in mild base transforms the molecules such that the major product is compound 21 which can be hydrolyzed to remove the protective groups, thereby generating DCI. Positions 1 and 6 are unaffected under these conditions, are thereby chemically anchored and thus dictate the stereochemistry of positions 2 and 5, respectively. (For purposes of this application, the numbering system for DCI is applied to its inosose precursors, which may be considered pro-DCI.) Since cis 6-5 fused ring dioxanes are more stable than the trans conformers, these positions should become cis to positions 1 and 6 and position 5 is duly epimerized. Positions 2 and 5, in turn, dictate the stereochemistry of positions 3 and 4 which should adopt a trans conformation, respectively. In conclusion, Raney nickel and base preferably yields chiroinositol since chemically anchoring strategic positions will preclude the formation of the myo- and scyllo- isomers. It should be noted that by starting with D-glucurone, L-chiroinositol formation is also precluded.

Figure 3:
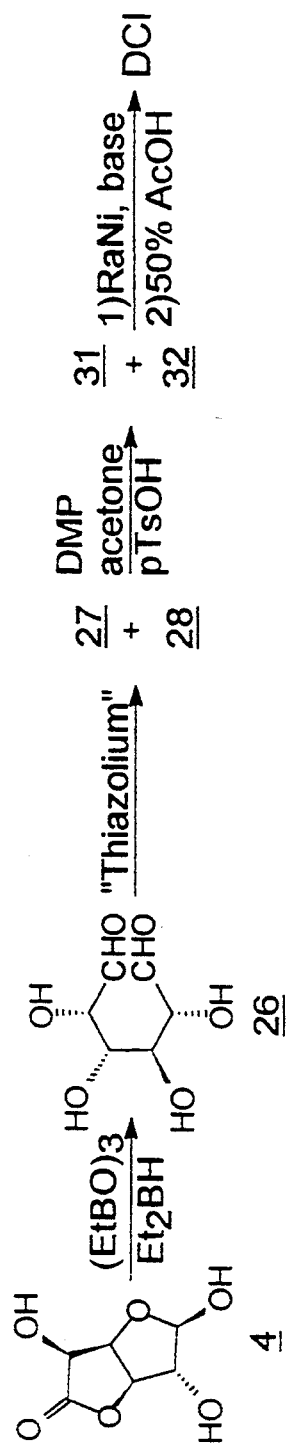
Figure 4:
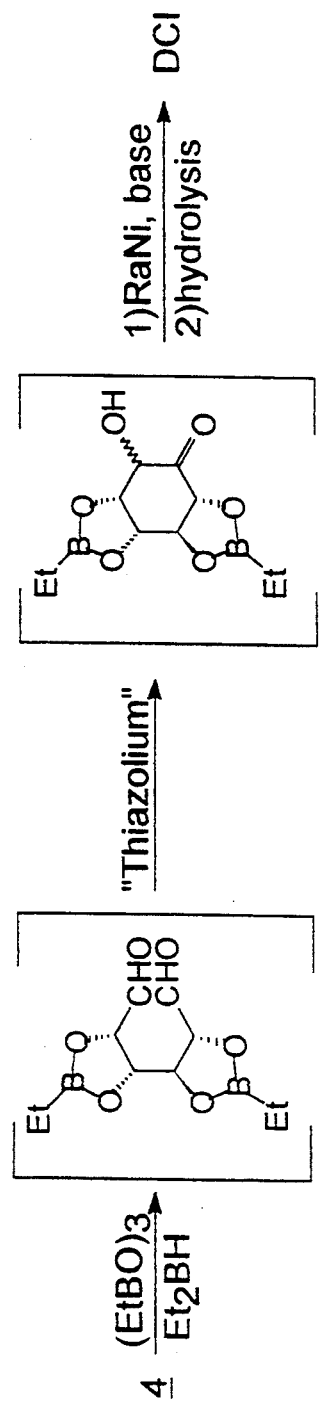
Figure 5:
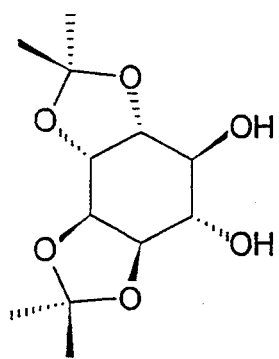

This total synthesis of DCI is shown in FIG. 3 and is done in 4 steps. It may be reduced to a one pot synthesis if one uses the boron protecting groups in step 1 to carry into the subsequent steps as shown in FIG. 4.

What is claimed is:

1. A method for the synthesis of D-chiro-inositol from glucodialdose, comprising the steps of:
   condensing the glucodialdose by an acyloin condensation reaction catalyzed by a thiazolium salt,
   protecting the carbon atoms at the 1, 2, 5 and 6 positions of the condensed compound by forming a first five-membered ring which incorporates carbons 1 and 2, and a second five membered ring which incorporates carbons 5 and 6,
   epimerizing the protected carbon at position 5 of the condensed compound by subjecting it to a weak base, reducing the ketone of the condensed compound under equilibrating conditions by refluxing it in the presence of Raney nickel, and
   removing the protecting groups by subjecting the compound to strong acid.

* * * * *